United States Patent [19]
Müller et al.

[11] Patent Number: 5,077,055
[45] Date of Patent: Dec. 31, 1991

[54] TOPICAL THERAPEUTIC SYSTEM COMPRISING 5-FLUOROURACIL

[75] Inventors: Walter Müller, Neuwied; Heinrich Kindel, Rengsdorf, both of Fed. Rep. of Germany

[73] Assignee: LTS Lohmann Therapie-Systeme GmbH & Co. KG, Neuwied, Fed. Rep. of Germany

[21] Appl. No.: 467,693

[22] Filed: Jan. 19, 1990

[30] Foreign Application Priority Data
Jan. 20, 1989 [DE] Fed. Rep. of Germany ....... 3901551

[51] Int. Cl.$^5$ .............................................. A61F 13/00
[52] U.S. Cl. ................................... 424/449; 424/448; 424/484; 424/486
[58] Field of Search ................ 424/448, 449, 484, 486

[56] References Cited
U.S. PATENT DOCUMENTS
3,769,071 10/1973 Trancik .............................. 424/448

Primary Examiner—Thurman K. Page
Assistant Examiner—D. Gabrielle Phelan
Attorney, Agent, or Firm—Sprung, Horn Kramer & Woods

[57] ABSTRACT

The present invention relates to a superficial therapeutic system consisting of an impermeable backing layer, an active substance containing matrix, and a removable protective layer, in which the matrix comprises:
a. antineoplastic active substance
b. a self-adhesive polyacrylate
c. a water absorber and optionally
d. a non-adhesive hydrophilic polyacrylate
e. a softener and/or penetration accelerator.

12 Claims, 4 Drawing Sheets

TOPICAL THERAPEUTIC SYSTEM COMPRISING 5-FLUOROURACIL

DESCRIPTION

The present invention relates to a topical therapeutic system comprising an anti-neoplastic active substance, particularly 5-fluorouracil.

Cytostatically and/or cytotoxically effective substances play an important role in medicine where excessive cell growth has to be regulated. Thus, their most common use is in the therapy of malignant tumors.

Applied locally they are also used in the therapy of less dangerous diseases, such as psoriasis, warts deriving from viruses, keratosis, Morbus Bowen, and basaliomes near the surface. Here the high local active substance concentrations necessary for a successful therapy are achieved without having to accept the side-effects occurring in the systemic chemotherapy of malignant tumors, which may enforce interruption of the therapy and sometimes result in deaths. Two locally applicable ointments containing 5-fluorouracil are commercially available (Effudix and Effluderm, both of Hoffmann-La Roche AG).

5-fluorouracil belongs to the so-called anti-metabolites, and in particular is a pyrimidine anti-metabolite.

Clinical experiences with this active substance as topical cytostatic have been known for about 25 years.

It is particularly appreciated due to its good medical and cosmetic results (Goette, D. K.; J. AM. ACAD. DERMATOL: 4: 633-649, 1981).

However, the application in form of ointments bears the disadvantage that it is difficult—if not impossible—to provide a certain skin area over the whole period of treatment, which may last for several weeks, with a sufficient dose on the one hand, and, on the other hand, not to overdose the active substance.

This disadvantage was realized in U.S. Pat. No. 3,734,097 and led to an application system described therein. This system consists of a self-adhesive, areal drug-containing formulation which is provided on the one side with a supporting foil impermeable to active substances and auxiliaries, and on the other side with a foil having the same properties but which additionally may be removed prior to use.

U.S. Pat. No. 3,769,071 has the same background, here polyurethanes are used as carrier material for the substances 5-fluorouracil.

Thus, it is an object of the present invention to develop a system on this basis, which system exhibits all advantages of the known formulations, contains additional improvements and proves successful in practical tests.

During the treatment with cytostatically and cytotoxically effective substances, those cells having an increased division activity are gradually damaged more seriously than those which divide normally. It is a desired and necessary consequence for the success of the therapy that an increased death of those cells being active in dividing occurs at the place of application. This increased cell death is accompanied by inflammatory processes which in turn are accompanied by exudation of wound secretions. This increased wound exudation makes it difficult to maintain a certain skin area under occlusive conditions over a longer period of time without the system losing its contact to the skin. Solutions to this problem, such as providing edges extending the active substance containing part of the system, are not optimal, since they enlarge the total surface of the system and thus complicate the application, particularly if used in the face area.

Surprisingly it was found that this object can be achieved if the polymeric active substance carrier is rendered as polar as possible, and if an additional so-called water-absorber is added.

As relatively polar self-adhesive basic polymer a polyacrylate was used, since this class of adhesive has been used in the medical field for various applications and is regarded as very well accepted by the skin. Particularly suitable was the polyacrylate adhesive Durotak 280-2516 of National Starch.

As polar non-adhesive polyacrylates those are suitable which have a certain content of the following free polar groups: hydroxy groups, carboxyl groups, amino groups, quaternary ammonium groups, etc.

Very suitable for this purpose are, e.g., the polyacrylates of the Eudragit-series of Röhm-Pharma, since they have been applied in the tablet technology and may be regarded as physiologically acceptable. Particularly suitable is Eudragit RL 100 which chemically may be described as a copolymer of acrylic and methacrylic acid esters having a certain amount of quaternary ammonium groups. It is characterized by the fact that it mainly swells independently from the pH-value and for this fact alone supports the absorption of humidity into the system. Furthermore, it compensates to some extent for the softening effect of additional auxiliaries, such as 1,2-propanediol.

A variety of products on the basis of natural and synthetic polymers are offered as water-absorbers on the market. Water-absorbers on the basis of slightly cross-linked, pre-neutralized polyacrylic acids have proved to be suitable. The best results were achieved with the product Aquakeep 10 SH of Seitetsu Kagaku. As a matter of fact, due to their cross-linkage these water-absorbers do not dilute homogeneously in the plaster matrix, however, do not negatively influence the cohesion and adhesiveness of the matrix if used in a sufficient amount.

The backing layer may consist of flexible or non-flexible material, and may be one or multi-layered. Substances suitable for their production are polymeric substances, such as, e.g., polyethylene, polypropylene, polyvinyl chloride, polyethylene terephthalate, and polyamide. As further materials metal foils, such as aluminum foils alone or coated with a polymeric substance, may be used as well. A preferred embodiment is a polyethylene terephthalate foil having a thickness of $10\mu$, which is aluminized on the matrix side, and has a skin colored dye on that side lying outside after application.

The removable protective layer, which is in contact with the self-adhesive matrix and is removed prior to application, e.g., consists of the same materials as are used for the production of the cover layer, provided that they are rendered removable, e.g. by way of a silicone treatment. Further detachable protective layers, e.g., are polytetrafluoroethylene, treated paper, cellophane, and the like.

The invention will be further described with reference to the accompanying drawings wherein.

Figure 1:
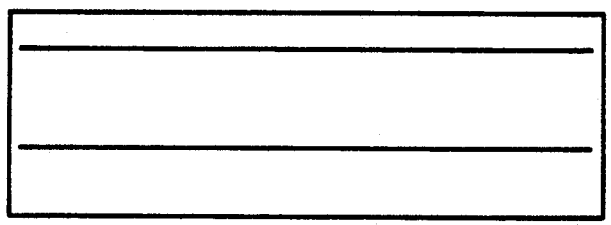
FIG. 1 is a schematic side elevation of a system in accordance with the invention.
Figure 2:
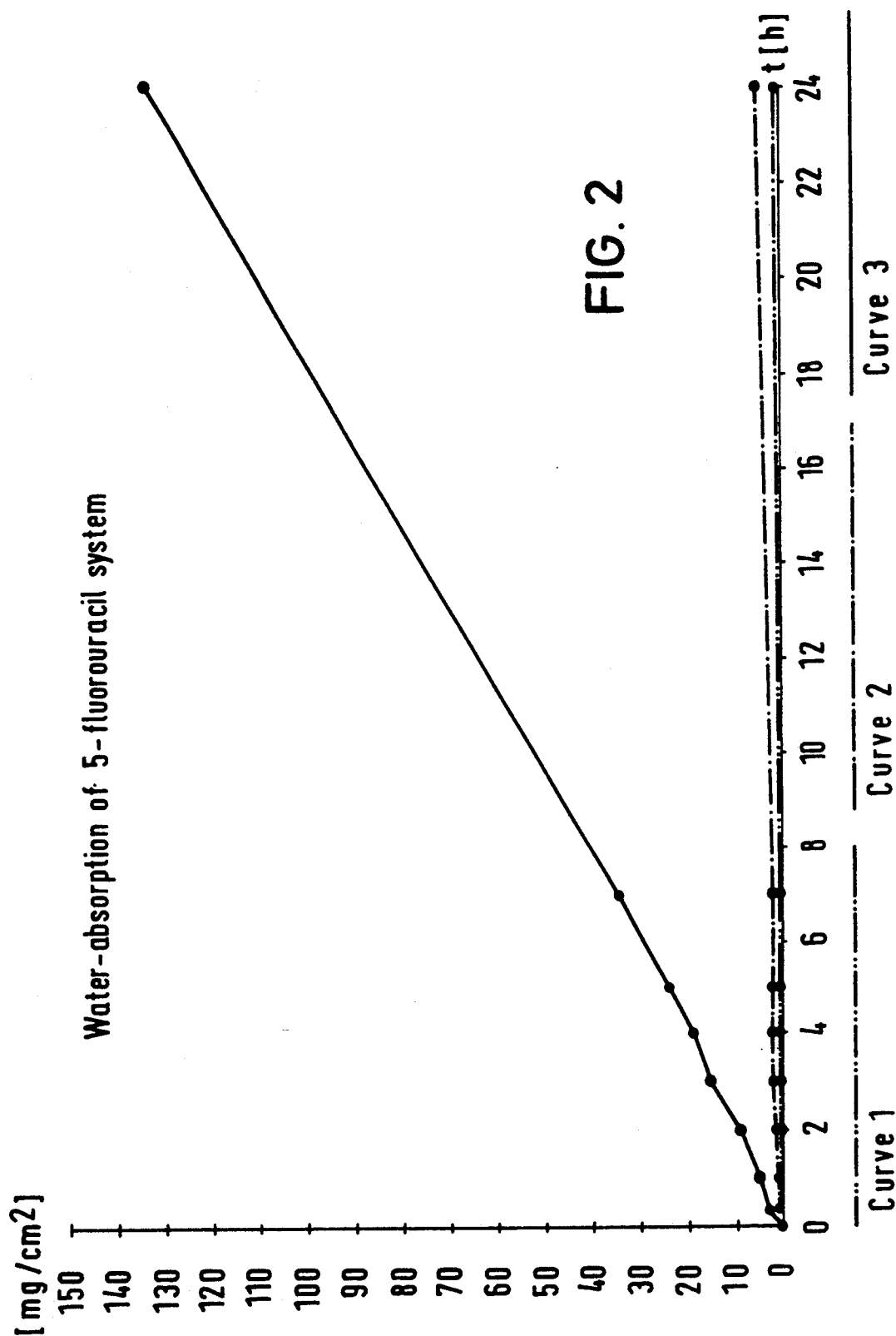
FIG. 2 is a plot showing the effect of certain additives on water absoprtion.

FIG. 1 shows in side elevation a system in the sense of the present invention. FIG. 2 shows the increase of the water absorption of the acrylate adhesive by the addition of Eudragit RL 100 and Aquakeep 10 SH. Curve 1 shows the water absorption of the pure acrylate adhesive, which may practically be disregarded, curve 2 demonstrates the slight increase by the addition of Eudragit RL 100, and curve 3 the drastic increase by the addition of Aquakeep 10 SH.

Curve 3 is based on the following matrix formulation resulting after removal of the solvent; said formulation has proved to be very effective in clinical tests:

7910 g Polyacrylate adhesive (Durotak 280-2516 of National Starch)
1980 g Copolymer of acrylic and methacrylic acid esters having a certain content of quaternary ammonium groups (Eudragit RL 100 of Röhm-Pharma)
500 g Water absorber on the basis of cross-linked neutralized polyacrylic acid (Aquakeep 10 SH of Seitetsu Kagaku)
1040 g 1,2-propanediol
85 g 5-Fluorouracil
Weight per unit area: 115 g/m$^2$ Curves 2 and 1 are based on the same formulation and the same weight per unit area, however without the addition of Aquakeep 10 SH or without Aquakeep 10 SH and Eudragit RL 100, respectively.

The measurements were carried out at 32° C. with demineralized water, the water absorption was determined gravimetrically.

Figure 3:
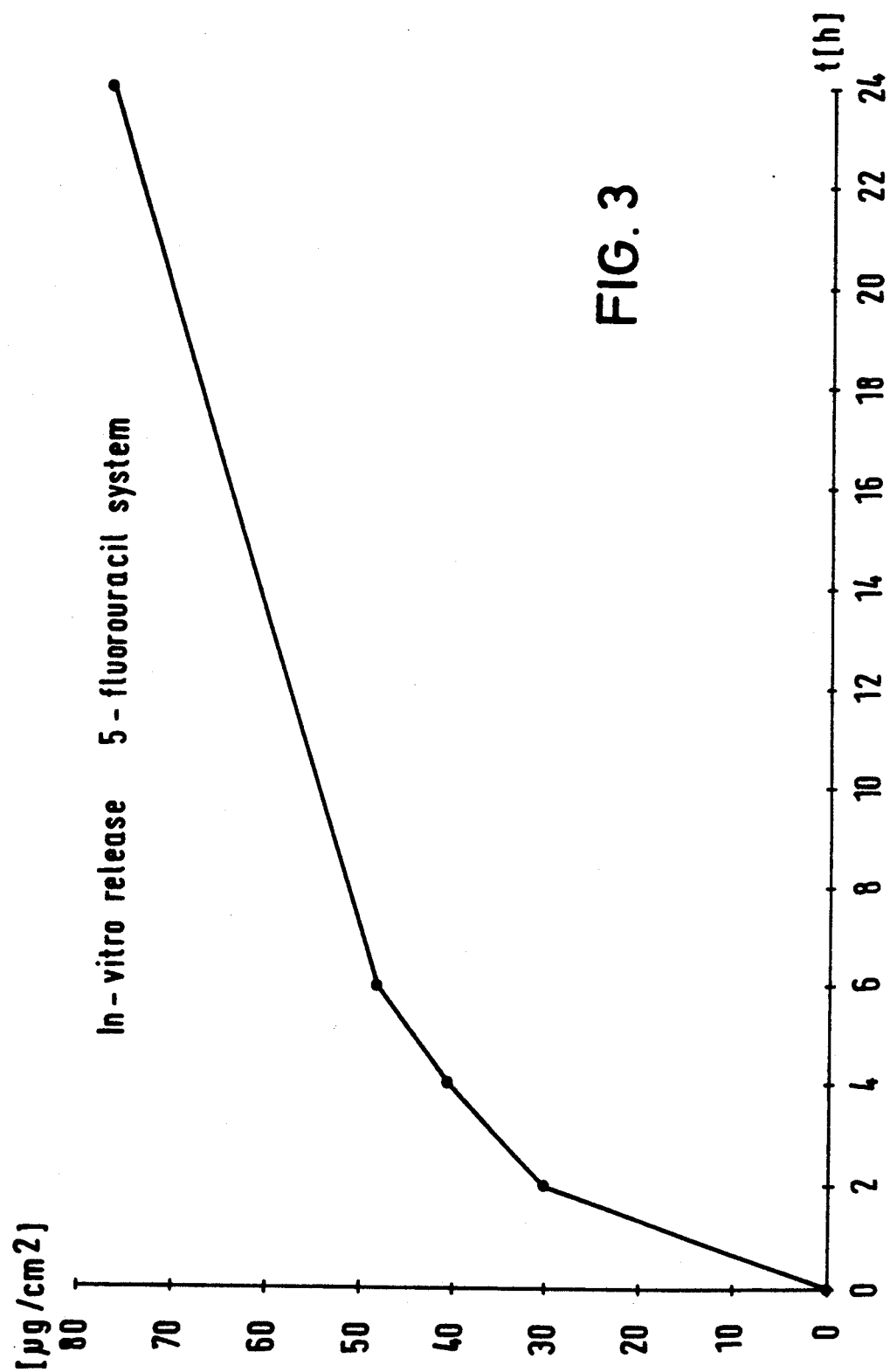
FIG. 3 is a plot showing the in vitro release of active material in accordance with the invention.

FIG. 3 shows the in-vitro release of a sample on the basis of the above mentioned formulation. The content of active substance amounts to 85 μg/cm$^2$. The release curve shows a course which is typical for matrix systems.

The release was carried out by means of a "rotating bottle" device at 32° C. using physiological saline as release medium; the active substance concentration in the test solutions was determined photometrically.

Clinical tests with 8 patients having the indication of actinic keratosis were carried out with systems having the same matrix formulation, circular form and a size of 1.13 cm$^2$. In all cases a success of the therapy could be observed after application of 6-7 systems. The systems were changed every 2 to 3 days.

Figure 4:
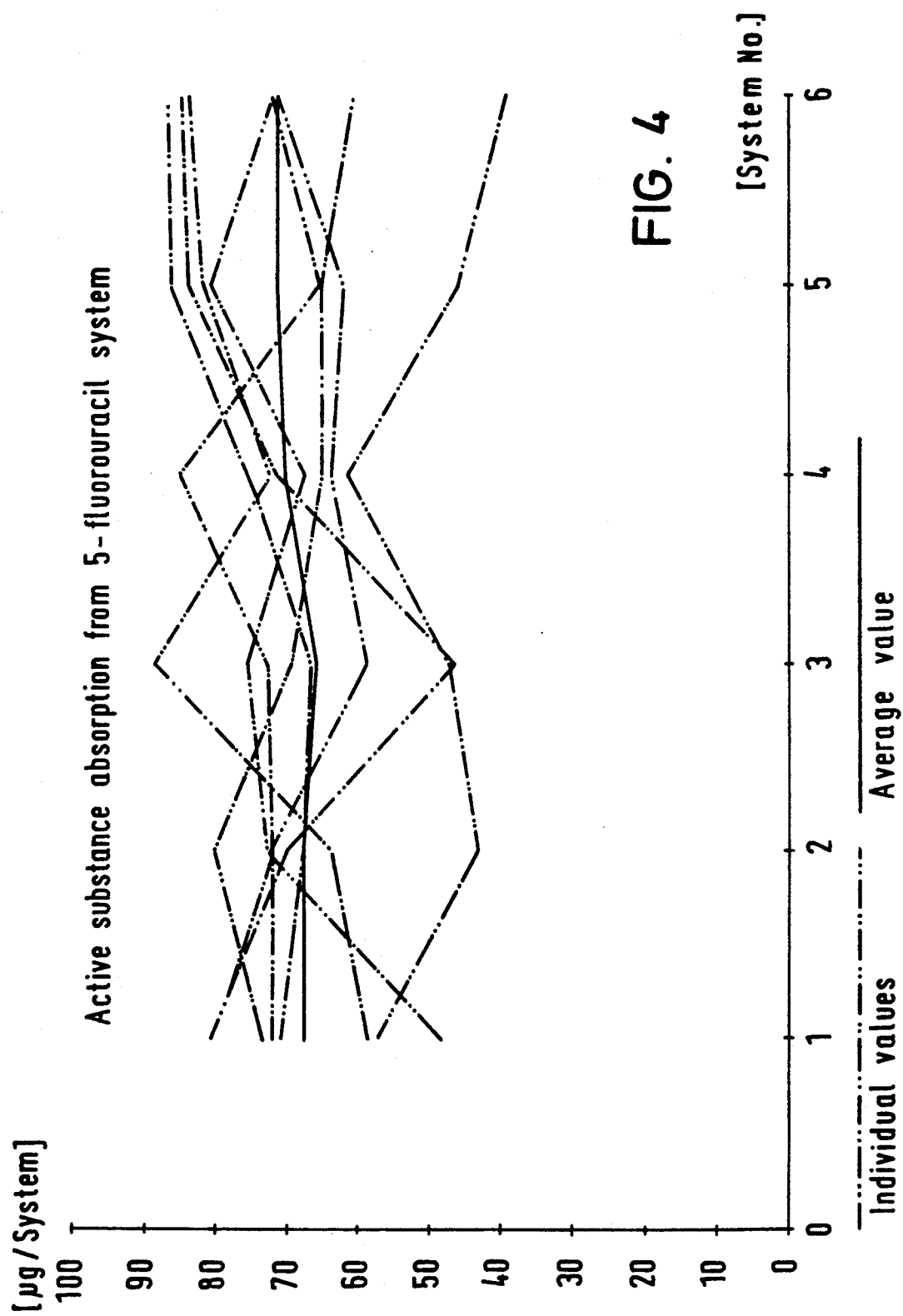
FIG. 4 is a plot showing adsorption of 5-fluorouracil from the novel system.

FIG. 4 shows the absorption of 5-fluorouracil from the systems; it was determined by residue determination of the active substance in the used systems.

69.5% or 63.8 μg, respectively, of the incorporated 91.8 μg 5-fluorouracil were absorbed on average (calculated from the tests with 8 patients and 6 systems per patient) during an application of the systems of 2 or 3 days. This corresponds to an average active substance absorption of approximately 30 μg 5-fluorouracil per patient, day, and system. In the case of such an extremely low active substance absorption, systemically toxic side-effects can definitely be excluded.

The special advantages of the present invention are summed up again in the following:
a. reliable therapeutic effect with minimal active substance absorption
b. short period of treatment
c. the active substance is merely applied to the area to be treated
d. high water absorption capacity of the system
e. phototoxic reactions are suppressed by occlusive conditions
f. good cosmetic results
g. considerably improved acceptance by the patient due to the necessity of applying a new system only every 2-3 days (ointment twice a day).

EXAMPLE

Method to Produce an Approximately 100 m$^2$ of a 5-fluorouracil Superficial Therapeutic System 4,352 g of a 40% (weight per weight basis) solution of a copolymer of acrylic and methacrylic acid esters having a certain amount of quanternary ammonium groups (Eudragit RL 100 of Röhm-Pharma) in methylethyl ketone are added under stirring to 16,697.8 g of a 42% (weight per weight basis) solution of a polyacrylate adhesive (Durotak 280-2516 of National Starch); 436 g water absorber on the basis of cross-linked, neutralized polyacrylic acid (Aquakeep 10 SH of Seitetsu Kagaku, particle size ≦ 125 μm) and subsequently a solution of 75 g 5-fluorouracil in 2,753 g 1,2-propanediol are added.

This mass is coated on an aluminized and siliconized polyester foil having a thickness of 100μ, so that after removal of the solvent a film having an area weight of 115 g/m$^2$ results. This film is covered with a polyester foil having a thickness of 10μ, cut into pieces of desired size and punched.

Accordingly, there has been provided a superficial, i.e. topical, therapeutic system comprising an impermeable backing layer, an active substance containing matrix and a removable protective layer, the matrix comprising:

a) an anti-neoplastic active substance, preferably 5-fluorouracil present in 0.2-5, preferably 0.3-1% and most preferably 0.6-0.9%, by weight, b) a self-adhesive polyacrylate present in at least 50%, preferably 65-75%, by weight, c) a water absorber present in 1-15%, preferably 1-10% and most preferably 4-5%, by weight, d) a non-adhesive hydrophilic polyacrylate present in 0-48.8%, preferably 10-35% and most preferably 15-25%, by weight, and e) a softener and/or penetration accelerator present in 0-20%, preferably 1,2-propanediol present in 5-15% and most preferably 5-10%, by weight.

The matrix may have a circular shape and a diameter of 0.5-3 cm. preferably 1-2 cm and more preferably 1-1.3 cm. Alternatively it may be rectangular in shape with an area of 1 to 200, preferably 1 to 50 and most preferably 2 to 20, cm$^2$.

We claim:

1. A topical therapeutic system comprising an impermeable backing layer, an active substance containing matrix and a removable protective layer, the matrix comprising:
a) 5-fluorouracil
b) a self-adhesive polyacrylate
c) a water absorber based on cross-linked neutralized polyacrylic acid,
and optionally
d) a non-adhesive hydrophilic polyacrylate and/or
e) a softener and/or penetration accelerator.

2. A topical therapeutic system according to claim 1, wherein the matrix comprises by weight:
a) 0.2-5% of 5-fluorouracil,
b) at least 50% of a self-adhesive polyacrylate, c) 1-15% of the water absorber,
d) 0-48.8% of a non-adhesive hydrophilic polyacrylate, and
e) 0-20% of a softener and/or penetration accelerator.

3. A topical therapeutic system according to claim 1, wherein the matrix comprises by weight:
a) 0.3-1% of 5-fluorouracil,
b) 65-75% of a self-adhesive polyacrylate,
c) 1-10% of the water absorber,
d) 10-35% of a non-adhesive hydrophilic polyacrylate, and
e) 5-15% of a softener and/or penetration accelerator.

4. A topical therapeutic system according to claim 1, wherein the matrix comprises by weight:
a) 0.6-0.9% of 5-fluorouracil,
b) 65-75% of a self-adhesive polyacrylate,
c) 4-5% of the water absorber,
d) 15-25% of a non-adhesive hydrophilic polyacrylate, and
e) 5-10% of a softener and/or penetration accelerator.

5. A topical therapeutic system according to claim 1, wherein (e) is 1,2-propanediol.

6. A topical therapeutic system according to claim 1, wherein the matrix has a circular shape and a diameter of 0.5-3 cm.

7. A topical therapeutic system according to claim 1, wherein the matrix has a circular shape and a diameter of 1-2 cm.

8. A topical therapeutic system according to claim 1, wherein the matrix has a circular shape and a diameter of 1-1.3 cm.

9. A topical therapeutic system according to claim 1, wherein the matrix has a rectangular shape and an area of 1 to 200 cm$^2$.

10. A topical therapeutic system according to claim 1, wherein the matrix has a rectangular shape and an area of 1 to 50 cm$^2$.

11. A topical therapeutic system according to claim 1, wherein the matrix has a rectangular shape and an area of 2 to 20 cm$^2$.

12. A topical therapeutic system according to claim 1, wherein the water absorber (c) is not homogeneously diluted in the matrix.

* * * * *